United States Patent
Nakayama et al.

(12) 
(10) Patent No.: US 11,692,986 B2
(45) Date of Patent: *Jul. 4, 2023

(54) SENSOR ELEMENT AND GAS SENSOR

(71) Applicant: NGK INSULATORS, LTD., Aichi (JP)

(72) Inventors: Yuki Nakayama, Nagoya (JP); Shota Kageyama, Nagoya (JP); Yusuke Fujii, Nagoya (JP); Kei Kosaka, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/826,284

(22) Filed: May 27, 2022

(65) Prior Publication Data

US 2022/0308031 A1 Sep. 29, 2022

Related U.S. Application Data

(63) Continuation of application No. 16/658,340, filed on Oct. 21, 2019, now Pat. No. 11,474,089, which is a (Continued)

(30) Foreign Application Priority Data

Feb. 6, 2018 (JP) .................................. 2018-019444

(51) Int. Cl.
  *G01N 33/00* (2006.01)
  *G01N 27/419* (2006.01)
  *G01N 27/407* (2006.01)

(52) U.S. Cl.
  CPC ....... *G01N 33/0036* (2013.01); *G01N 27/419* (2013.01); *G01N 27/4077* (2013.01)

(58) Field of Classification Search
  CPC .. G01N 27/4077; G01N 27/41; G01N 27/419; G01N 33/0036
  See application file for complete search history.

(56) References Cited

U.S. PATENT DOCUMENTS 9,080,964 B2 * 7/2015 Otsuka ............... G01N 33/0014
9,476,863 B2 * 10/2016 Sakuma ............ G01N 27/4072
(Continued)

FOREIGN PATENT DOCUMENTS

JP  2007-278945 A  10/2007
JP  2007-285961 A  11/2007
(Continued)

OTHER PUBLICATIONS

International Search Report of PCT/JP2019/001849 dated Apr. 23, 2019.
(Continued)

*Primary Examiner* — John Fitzgerald
*Assistant Examiner* — Gedeon M Kidanu
(74) *Attorney, Agent, or Firm* — Mattingly & Malur, PC

(57) ABSTRACT

A sensor element includes element main body including side surfaces, a detection unit, connector electrodes disposed on the rear end-side part of the side surfaces, a porous layer that covers at least front end-side part of the side surface, the porous layer having a porosity of 10% or more, and a water-penetration reduction portion. The water-penetration reduction portion is disposed on the side surface so as to divide the porous layer or to be located closer to the rear end than the porous layer. The length L of the water-penetration reduction portion is 0.5 mm or more. The water-penetration reduction portion includes, among a dense layer covering the side surface and having a porosity of less than 10% and a gap region in which the porous layer is absent, at least the dense layer. The water-penetration reduction portion reduces the capillarity of water.

15 Claims, 4 Drawing Sheets

Related U.S. Application Data continuation of application No. PCT/JP2019/001849, filed on Jan. 22, 2019.

(56) References Cited

U.S. PATENT DOCUMENTS

| | | | | |
|---|---|---|---|---|
| 10,161,900 | B2* | 12/2018 | Ishikawa | G01N 27/4077 |
| 2007/0235332 | A1* | 10/2007 | Sugiyama | G01N 27/4075 |
| | | | | 204/424 |
| 2007/0246359 | A1 | 10/2007 | Sugiyama et al. | |
| 2009/0242404 | A1 | 10/2009 | Miyashita et al. | |
| 2012/0103808 | A1 | 5/2012 | Igarashi et al. | |
| 2012/0211362 | A1* | 8/2012 | On | G01N 27/4077 |
| | | | | 204/424 |
| 2014/0130572 | A1* | 5/2014 | Otsuka | G01N 27/4077 |
| | | | | 73/23.31 |
| 2015/0075254 | A1* | 3/2015 | Sakuma | G01N 27/4072 |
| | | | | 73/23.31 |
| 2015/0114085 | A1* | 4/2015 | Iwano | B05D 1/36 |
| | | | | 427/372.2 |
| 2015/0355142 | A1 | 12/2015 | Murakami et al. | |
| 2016/0054256 | A1* | 2/2016 | Sakuma | G01N 27/4071 |
| | | | | 204/408 |
| 2018/0217088 | A1 | 8/2018 | Tahira et al. | |
| 2018/0284055 | A1* | 10/2018 | Hino | G01N 27/41 |

FOREIGN PATENT DOCUMENTS

| | | | |
|---|---|---|---|
| JP | 2009-236833 | A | 10/2009 |
| JP | 2009-236835 | A | 10/2009 |
| JP | 2012-108104 | A | 6/2012 |
| JP | 2012-185113 | A | 9/2012 |
| JP | 2012185113 | A * | 9/2012 |
| JP | 2012-242112 | A | 12/2012 |
| JP | 2014-055859 | A | 3/2014 |
| JP | 2016-014659 | A | 1/2016 |
| JP | 2016-065852 | A | 4/2016 |
| JP | 2017-106874 | A | 6/2017 |
| JP | 2018-119901 | A | 8/2018 |

OTHER PUBLICATIONS

International Preliminary Report on Patentability received in corresponding International Application No. PCT/JP2019/001849 dated Aug. 20, 2020.
Japanese Office Action received in corresponding Japanese Application No. 2019-570654 dated Nov. 10, 2020.
Japanese Notice of Opposition received in corresponding Japanese Application No. 2021-700870 dated Oct. 8, 2021.
U.S. Appl. No. 16/669,555, filed Oct. 31, 2019.
U.S. Appl. No. 16/669,556, filed Oct. 31, 2019.

* cited by examiner

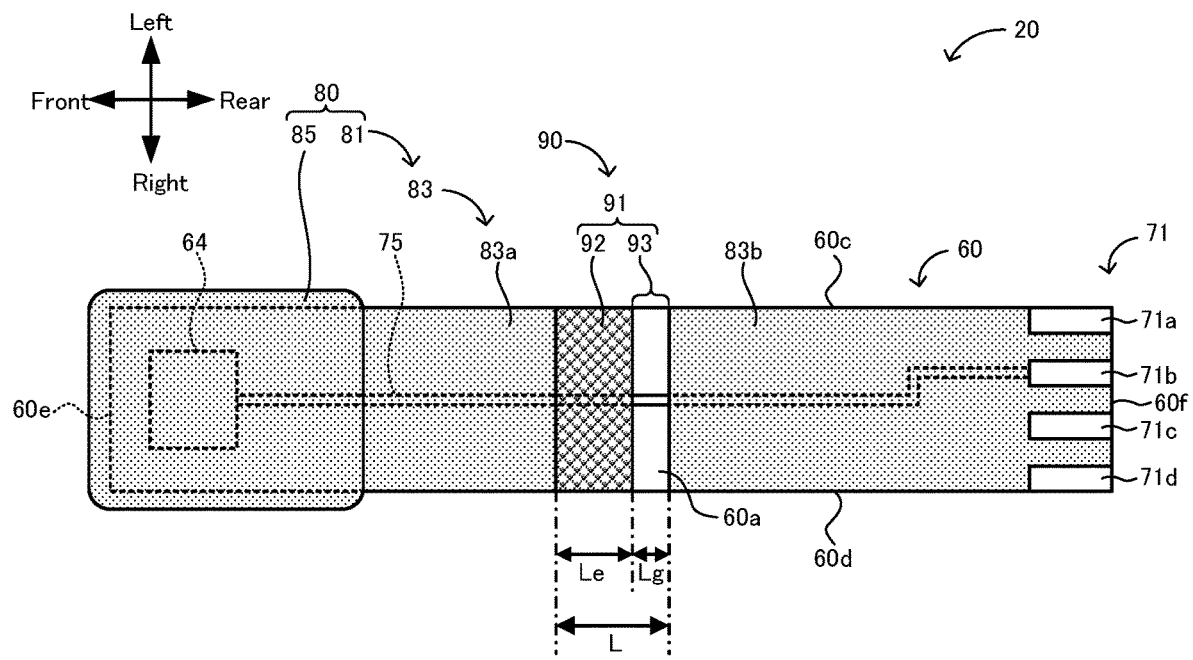
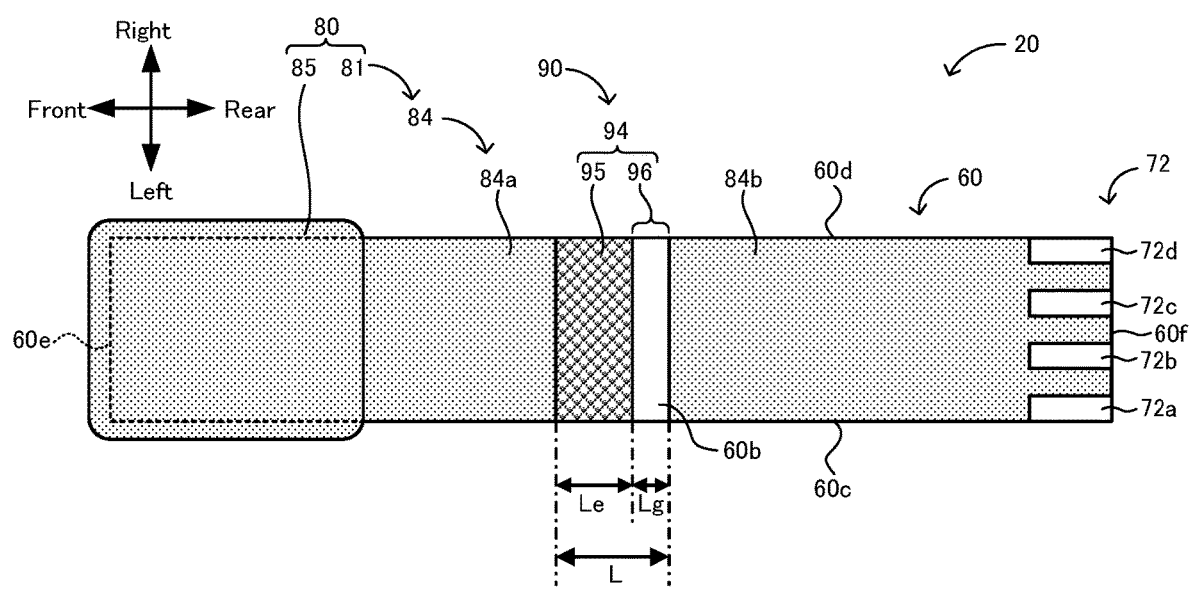

SENSOR ELEMENT AND GAS SENSOR

CROSS-REFERENCE TO RELATED APPLICATIONS

This application is a continuation application of U.S. application Ser. No. 16/658,340, filed Oct. 21, 2019, which is a continuation application of PCT/JP2019/001849, filed on Jan. 22, 2019, which claims the benefit of priority of Japanese Patent Application No. 2018-019444, filed on Feb. 6, 2018, the entire contents of which are incorporated herein by reference.

BACKGROUND OF THE INVENTION

1. Field of the Invention

The present invention relates to a sensor element and a gas sensor.

2. Description of the Related Art

Sensor elements that detect the specific gas concentration, such as NOx, in the measurement-object gas, such as an automotive exhaust gas, are known (e.g., PTL 1). The sensor element disclosed in PTL 1 includes a multilayer body that includes oxygen ion-conducting solid electrolyte layers stacked on top of one another. This sensor element also includes an outer pump electrode, a lead wire for the outer pump electrode, a connector electrode, and a porous protection layer, which are stacked on and above the upper surface of the multilayer body. The outer pump electrode, the lead wire for the outer pump electrode, and the connector electrode are connected to one another in this order and are in electrical conduction with one another. The connector electrode is electrically connected to the outside. The porous protection layer covers and protects the outer pump electrode and the lead wire for the outer pump electrode.

CITATION LIST

Patent Literature

PTL 1: Japanese Unexamined Patent Application Publication No. 2016-014659

SUMMARY OF THE INVENTION

When a porous layer similar to the porous protection layer described in PTL 1 is present on the surface of the sensor element, the moisture contained in an exhaust gas may move inside the porous layer by capillarity. As a result, the moisture may reach the connector electrode. In such a case, water and the components dissolved in water, such as sulfuric acid, cause rusting and corrosion of the connector electrode and a short circuit between the connector electrodes.

The present invention was made in order to address the above issues. An object of the present invention is to prevent the moisture from passing through the porous layer and reaching the connector electrodes.

Solution to Problem

The present invention employs the following structures in order to achieve the object.

A sensor element of the present invention includes:

a long-length element main body including front and rear ends and one or more side surfaces, the front and rear ends being ends of the element main body in a longitudinal direction of the element main body, the one or more side surfaces being surfaces extending in the longitudinal direction;

a detection unit including a plurality of electrodes disposed in the front end-side part of the element main body, the detecting unit detecting the specific gas concentration in the measurement-object gas;

one or more connector electrodes disposed on the rear end-side part of any of the one or more side surfaces, the one or more connector electrodes being in electrical conduction with the outside;

a porous layer that covers at least the front end-side part of the side surface on which the one or more connector electrodes are disposed, the porous layer having a porosity of 10% or more; and a water-penetration reduction portion disposed on the side surface so as to divide the porous layer in the longitudinal direction or to be located closer to the rear end than the porous layer, the water-penetration reduction portion being located closer to the front end than the one or more connector electrodes, the length L of the water-penetration reduction portion in the longitudinal direction being 0.5 mm or more, the water-penetration reduction portion including, among a dense layer covering the side surface and having a porosity of less than 10% and a gap region in which the porous layer is absent, the gap region being arranged adjacent to the dense layer, at least the dense layer, the water-penetration reduction portion reducing the capillarity of water in the longitudinal direction.

In the above-described sensor element, the connector electrodes are disposed on a rear end-side part of any of the one or more side surfaces of the element main body, and the porous layer is arranged to cover at least the front end-side part of the side surface. Furthermore, the sensor element includes the water-penetration reduction portion disposed on the side surface so as to divide the porous layer in the longitudinal direction or to be located closer to the rear end than the porous layer. The water-penetration reduction portion is located closer to the front end than the connector electrode. Therefore, even when the front end-part of the element main body, in which a plurality of electrodes constituting the detection unit are present, is exposed to the measurement-object gas and the moisture contained in the measurement-object gas moves inside the porous layer toward the rear end of the element main body by capillarity, the moisture reaches the water-penetration reduction portion before reaching the connector electrodes. In the water-penetration reduction portion, which includes, of the dense layer and the gap region, at least the dense layer, the capillarity of water in the longitudinal direction of the element main body is not likely to occur, unlike in the porous layer. In addition, since the length L of the water-penetration reduction portion in the longitudinal direction is 0.5 mm or more, the likelihood of the moisture passing through the water-penetration reduction portion can be reduced to a sufficient degree. By the above mechanisms, the water-penetration reduction portion reduces the likelihood of the moisture passing through the water-penetration reduction portion and reaching the connector electrodes. Accordingly, the above sensor element is capable of reducing the likelihood of the moisture passing through the porous layer and reaching the connector electrodes. In the above case, the porosity of the dense layer may be 8% or less or may be 5% or less.

In the sensor element according to the present invention, the length Le of the dense layer in the longitudinal direction may be 0.5 mm or more. In such a case, the likelihood of the moisture passing through the water-penetration reduction portion in the longitudinal direction can be reduced to a sufficient degree by using only the dense layer of the water-penetration reduction portion.

In the sensor element according to the present invention, the length Le of the dense layer in the longitudinal direction may be 20 mm or less. In such a case, for example, in the case where the element main body and the dense layer are prepared by baking an unbaked element main body and an unbaked dense layer, the warpage of the sensor element due to the difference in shrinkage ratio during baking between the unbaked element main body and the unbaked dense layer can be reduced.

In the sensor element according to the present invention, the length Le of the dense layer in the longitudinal direction may be 30% or less of the length of the element main body in the longitudinal direction. In such a case, for example, in the case where the element main body and the dense layer are prepared by baking an unbaked element main body and an unbaked dense layer, the warpage of the sensor element due to the difference in shrinkage ratio during baking between the element main body and the dense layer can be reduced.

In the sensor element according to the present invention, the length Lg of the gap region in the longitudinal direction may be 1 mm or less. In such a case, since the length Lg of the gap region is relatively small, the area of a part of the side surface of the element main body which is exposed to the outside (the part that is not covered with any of the porous layer and the dense layer) can be reduced.

In the sensor element according to the present invention, the water-penetration reduction portion does not necessarily include the gap region. In other words, the length Lg of the gap region of the water-penetration reduction portion in the longitudinal direction may be 0 mm. In such a case, the area of a part of the side surface of the element main body which is exposed to the outside (the part that is not covered with any of the porous layer and the dense layer) can be further reduced.

The sensor element according to the present invention may further include an outer lead portion disposed on the side surface on which the one or more connector electrodes are disposed, the outer lead portion providing conduction between any of the electrodes and the one or more connector electrodes. The porous layer may cover at least a part of the outer lead portion. This enables at least a part of the outer lead portion to be protected with the porous layer. In the case where the outer lead portion is protected with the porous layer, the porous layer is likely to be disposed at a position close to the one or more connector electrodes and, therefore, it is meaningful to apply the present invention to such a sensor element.

In the above case, the porous layer may cover the entirety of the outer lead portion. Alternatively, the porous layer may cover the entirety of the part of the outer lead portion on which the water-penetration reduction portion is not present. The sensor element according to the present invention may include an outer electrode that is one of the electrodes included in the detection unit, the outer electrode being in conduction with the connector electrodes via the outer lead portion and disposed on the side surface on which the connector electrodes are disposed. In such a case, the porous layer may cover the outer electrode.

In the sensor element according to the present invention, the porous layer may cover at least a region of the side surface on which the one or more connector electrodes are disposed, the region extending from the front end of the side surface to the front end-side edge of the one or more connector electrodes, the region excluding a region in which the water-penetration reduction portion is present, and the water-penetration reduction portion may be disposed on the side surface so as to divide the porous layer in the longitudinal direction.

In the sensor element according to the present invention, the element main body may have a rectangular cuboid shape and four side surfaces that are surfaces extending in the longitudinal direction, one or more connector electrodes may be disposed on each of first and second side surfaces of the four side surfaces, the first and second side surfaces facing each other, the porous layer may cover each of the first and second side surfaces, and the water-penetration reduction portion may be disposed on each of the first and second side surfaces. In the above case, the element main body may be a multilayer body constituted by a plurality of layers stacked on top of one another, and the first and second side surfaces may be the upper and lower surfaces of the element main body when the direction in which the layers are stacked is considered the top-to-bottom direction.

The gas sensor according to the present invention includes the sensor element according to any one of the above-described aspects. Therefore, the gas sensor has the same advantageous effects as the above-described sensor element according to the present invention. That is, for example, the gas sensor is capable of reducing the likelihood of the moisture passing through the porous layer and reaching the connector electrodes.

BRIEF DESCRIPTION OF THE DRAWINGS

FIG. 4 is a top view of a sensor element 20.

FIG. 5 is a bottom view of a sensor element 20.

DETAILED DESCRIPTION OF THE INVENTION

Figure 1:
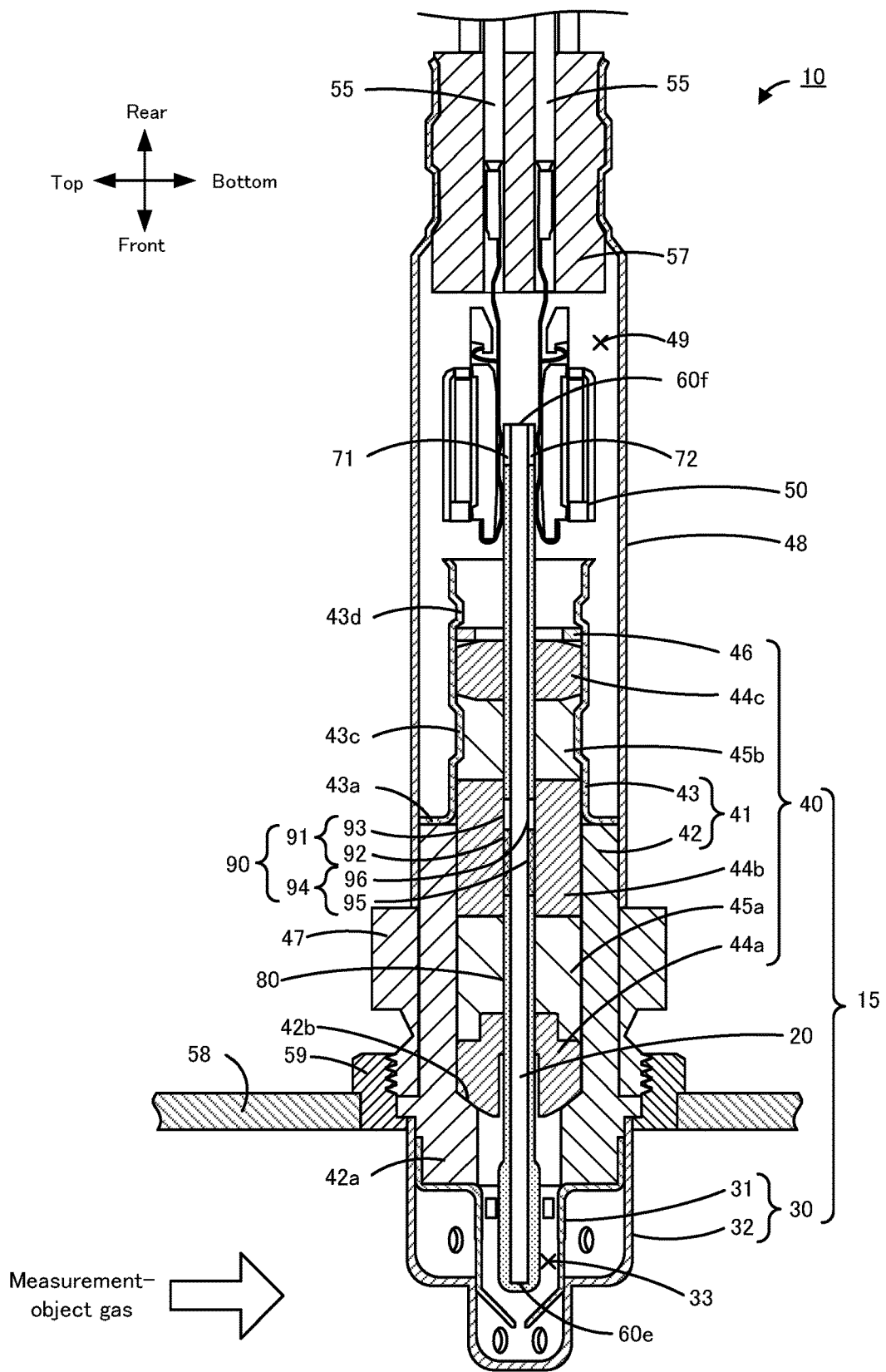
FIG. 1 is a longitudinal cross-sectional view of a gas sensor 10 attached to a pipe 58.
Figure 2:
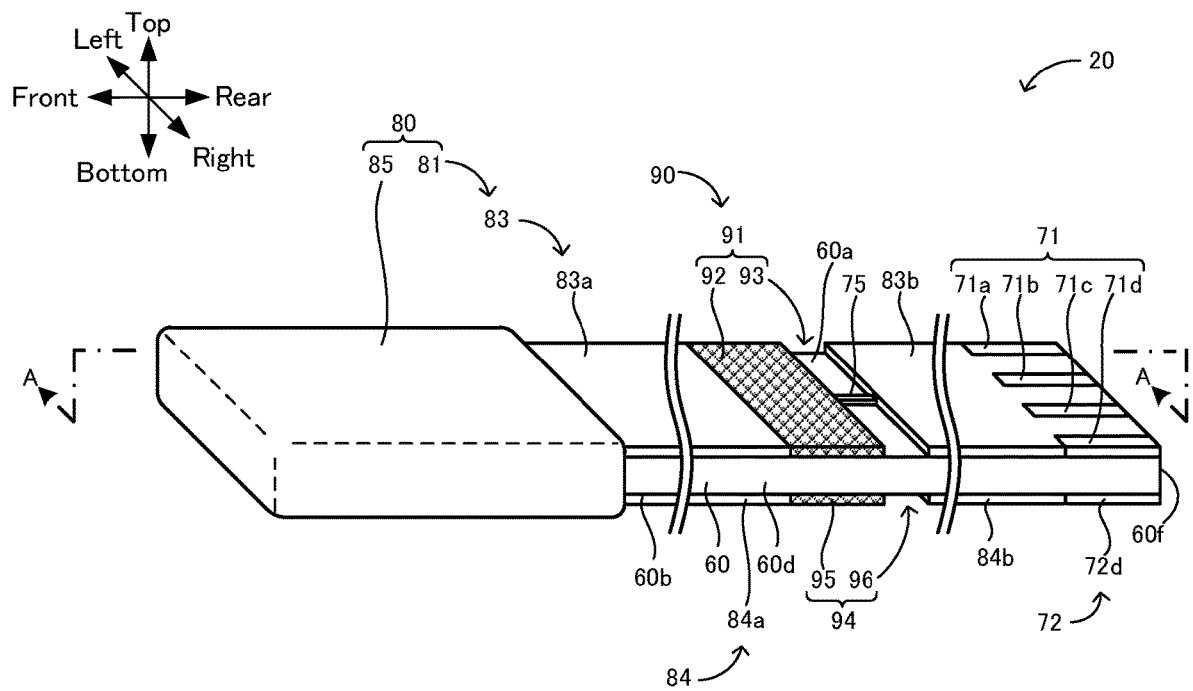
FIG. 2 is a perspective view of a sensor element 20.
Figure 3:
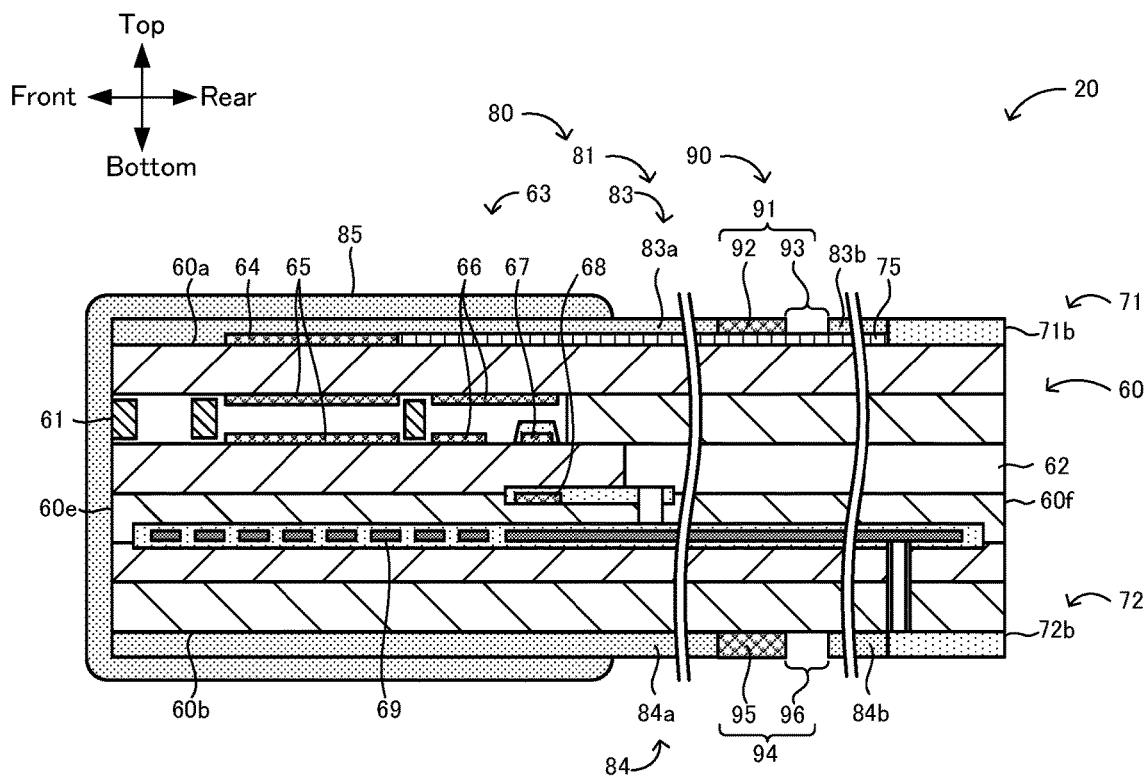
FIG. 3 is a cross-sectional view taken along the line A-A in FIG. 2.

Embodiments of the present invention are described below with reference to the attached drawings. FIG. 1 is a longitudinal cross-sectional view of a gas sensor 10 according to an embodiment of the present invention which is attached to a pipe 58. FIG. 2 is a perspective view of a sensor element 20 viewed from the upper right front. FIG. 3 is a cross-sectional view taken along the line A-A in FIG. 2. FIG. 4 is a top view of the sensor element 20. FIG. 5 is a bottom view of the sensor element 20. In this embodiment, as illustrated in FIGS. 2 and 3, the longitudinal direction of the element main body 60 included in the sensor element 20 is referred to as "front-to-rear direction" (length direction), the direction in which the layers constituting the element main body 60 are stacked (thickness direction) is referred to as "top-to-bottom direction", and a direction perpendicular to the front-to-rear direction and the top-to-bottom direction is referred to as "left-to-right direction" (width direction).

As illustrated in FIG. 1, the gas sensor 10 includes an assembly 15, a nut 47, an external cylinder 48, a connector 50, lead wires 55, and a rubber stopper 57. The assembly 15 includes a sensor element 20, a protective cover 30, and an element-sealing member 40. The gas sensor 10 is attached to a pipe 58, such as an automotive exhaust gas pipe, and used for measuring the specific gas concentration, such as NOx or $O_2$, (particular gas concentration) in the exhaust gas, which is the gas to be analyzed. In this embodiment, the gas sensor 10 is a gas sensor that measures NOx concentration as a particular gas concentration. Among the ends (front and rear ends) of the sensor element 20 in the longitudinal direction, the front end-side part of the sensor element 20 is exposed to the measurement-object gas.

The protective cover 30 includes, as illustrated in FIG. 1, a hollow cylindrical inner protective cover 31 with a bottom which covers the front end-part of the sensor element 20 and a hollow cylindrical outer protective cover 32 with a bottom which covers the inner protective cover 31. Each of the inner and outer protective covers 31 and 32 has a plurality of holes formed therein, through which the measurement-object gas is passed. The space surrounded by the inner protective cover 31 serves as an element chamber 33. A fifth surface 60e (front end-side surface) of the sensor element 20 is located inside the element chamber 33.

The element-sealing member 40 is a member with which the sensor element 20 is sealed and fixed. The element-sealing member 40 includes a cylindrical body 41 including a main fitting 42 and an inner cylinder 43, insulators 44a to 44c, compacts 45a and 45b, and a metal ring 46. The sensor element 20 is located on the central axis of the element-sealing member 40 and penetrates the element-sealing member 40 in the front-rear direction.

The main fitting 42 is a hollow cylindrical member made of a metal. The front-side part of the main fitting 42 is a thick-wall portion 42a having a smaller inside diameter than the rear-side part of the main fitting 42. The protective cover 30 is attached to a part of the main fitting 42 which is on the same side as the front end-side of the sensor element 20 (front-side part of the main fitting 42). The rear end of the main fitting 42 is welded to a flange portion 43a of the inner cylinder 43. A part of the inner peripheral surface of the thick-wall portion 42a serves as a bottom surface 42b, which is a stepped surface. The bottom surface 42b holds the insulator 44a such that the insulator 44a does not protrude forward.

The inner cylinder 43 is a hollow cylindrical member made of a metal and includes the flange portion 43a formed at the front end of the inner cylinder 43. The inner cylinder 43 and the main fitting 42 are coaxially fixed to each other by welding. The inner cylinder 43 includes a diameter reduction portion 43c that presses the compact 45b toward the central axis of the inner cylinder 43 and a diameter reduction portion 43d that presses the insulators 44a to 44c and the compacts 45a and 45b in the downward direction in FIG. 1 with the metal ring 46 interposed therebetween, the diameter reduction portions 43c and 43d being formed in the inner cylinder 43.

The insulators 44a to 44c and the compacts 45a and 45b are interposed between the inner peripheral surface of the cylindrical body 41 and the sensor element 20. The insulators 44a to 44c serve as a support for the compacts 45a and 45b. Examples of the material for the insulators 44a to 44c include ceramics, such as alumina, steatite, zirconia, spinel, cordierite, and mullite, and glass. The compacts 45a and 45b are formed by, for example, molding a powder and serve as a sealing medium. Examples of the material for the compacts 45a and 45b include talc and ceramic powders, such as an alumina powder and boron nitride. The compacts 45a and 45b may include at least one of the above materials. The compact 45a is filled between the insulators 44a and 44b and pressed by the insulators 44a and 44b as a result of both (front and rear) ends of the compact 45a in the axial direction being sandwiched therebetween. The compact 45b is filled between the insulators 44b and 44c and pressed by the insulators 44b and 44c as a result of both (front and rear) ends of the compact 45b in the axial direction being sandwiched therebetween. The insulators 44a to 44c and the compacts 45a and 45b are sandwiched between the diameter reduction portion 43d and the metal ring 46, and the bottom surface 42b of the thick-wall portion 42a of the main fitting 42 and thereby pressed in the front-to-rear direction. As a result of the compacts 45a and 45b being compressed between the cylindrical body 41 and the sensor element 20 by the pressing force applied by the diameter reduction portions 43c and 43d, the compacts 45a and 45b seal the communication between the element chamber 33 formed inside the protective cover 30 and a space 49 created inside the external cylinder 48 and fix the sensor element 20.

The nut 47 is fixed to the outer surface of the main fitting 42 coaxially with the main fitting 42. The nut 47 includes a male thread portion formed in the outer peripheral surface of the nut 47. The male thread portion is inserted into a fixing member 59, which is welded to the pipe 58 and includes a female thread portion formed in the inner peripheral surface of the fixing member 59. This enables the gas sensor 10 to be fixed to the pipe 58 while the front end-side part of the sensor element 20 of the gas sensor 10 and the protective cover 30 of the gas sensor 10 are protruded toward the inside of the pipe 58.

The external cylinder 48 is a hollow cylindrical member made of a metal and covers the inner cylinder 43, the rear end-side part of the sensor element 20, and the connector 50. The upper part of the main fitting 42 is inserted into the external cylinder 48. The lower end of the external cylinder 48 is welded to the main fitting 42. A plurality of the lead wires 55, which are connected to the connector 50, are drawn from the upper end of the external cylinder 48 to the outside. The connector 50 is in contact with upper and lower connector electrodes 71 and 72 disposed on the rear end-side parts of the surfaces of the sensor element 20 and electrically connected to the sensor element 20. The lead wires 55 are in electrical conduction with electrodes 64 to 68 and a heater 69 disposed inside the sensor element 20 via the connector 50. The gap between the external cylinder 48 and the lead wires 55 is sealed with the rubber stopper 57. The space 49 inside the external cylinder 48 is filled with a reference gas. A sixth surface 60f (rear end-side surface) of the sensor element 20 is located inside the space 49.

The sensor element 20 includes an element main body 60, a detection unit 63, a heater 69, an upper connector electrode 71, a lower connector electrode 72, a porous layer 80, and a water-penetration reduction portion 90 as illustrated in FIGS. 2 to 5. The element main body 60 includes a multi-layer body constituted by a plurality of (6 layers in FIG. 3) oxygen ion-conducting solid-electrolyte layers composed of zirconia ($ZrO_2$) or the like which are stacked on top of one another. The element main body 60 has a long-length, rectangular cuboid shape, and the longitudinal direction of the element main body 60 is parallel to the front-to-rear direction. The element main body 60 has first to sixth surfaces 60a to 60f, which are the upper, lower, left, right, front, and rear outer surfaces of the element main body 60. The first to fourth surfaces 60a to 60d are surfaces that extend in the longitudinal direction of the element main body 60 and correspond to the side surfaces of the element main body 60. The fifth surface 60e is the front end-side surface of the element main body 60. The sixth surface 60f is the rear end-side surface of the element main body 60. The dimensions of the element main body 60 may be, for example, 25 mm or more and 100 mm or less long, 2 mm or more and 10 mm or less wide, and 0.5 mm or more and 5 mm or less thick. The element main body 60 includes a gas-to-be-analyzed introduction port 61 formed in the fifth surface 60e, through which the measurement-object gas is introduced into the element main body 60, and a reference gas introduction port 62 formed in the sixth surface 60f, through which a reference gas (in this embodiment, air) used as a reference for detecting the particular gas concentration is introduced into the element main body 60.

The detection unit 63 detects the specific gas concentration in the measurement-object gas. The detection unit 63 includes a plurality of electrodes disposed in the front end-side part of the element main body 60. In this embodiment, the detection unit 63 includes an outer electrode 64 disposed on the first surface 60a and an inner main pump electrode 65, an inner auxiliary pump electrode 66, a measurement electrode 67, and a reference electrode 68 that are disposed inside the element main body 60. The inner main pump electrode 65 and the inner auxiliary pump electrode 66 are disposed on the inner peripheral surface of a cavity formed inside the element main body 60 and have a tunnel-like structure.

Since the principle on which the detection unit 63 detects the specific gas concentration in the measurement-object gas is publicly known, detailed description is omitted herein. The detection unit 63 detects the particular gas concentration, for example, in the following manner. The detection unit 63 draws oxygen included in the measurement-object gas which is in the vicinity of the inner main pump electrode 65 to or from the outside (the element chamber 33) on the basis of the voltage applied between the outer electrode 64 and the inner main pump electrode 65. The detection unit 63 also draws oxygen included in the measurement-object gas which is in the vicinity of the inner auxiliary pump electrode 66 to or from the outside (the element chamber 33) on the basis of the voltage applied between the outer electrode 64 and the inner auxiliary pump electrode 66. This enables the measurement-object gas to reach a space around the measurement electrode 67 after the oxygen concentration in the gas has been adjusted to be a predetermined value. The measurement electrode 67 serves as a NOx-reducing catalyst and reduces the particular gas (NOx) included in the measurement-object gas. The detection unit 63 converts an electromotive force generated between the measurement electrode 67 and the reference electrode 68 in accordance with the oxygen concentration in the reduced gas or a current that flows between the measurement electrode 67 and the outer electrode 64 on the basis of the electromotive force into an electrical signal. The electrical signal generated by the detection unit 63 indicates the value reflective of the particular gas concentration in the measurement-object gas (the value from which the particular gas concentration can be derived) and corresponds to the value detected by the detection unit 63.

The heater 69 is an electric resistor disposed inside the element main body 60. Upon the heater 69 being fed with power from the outside, the heater 69 generates heat and heats the element main body 60. The heater 69 is capable of heating the solid-electrolyte layers constituting the element main body 60 and conserving the heat such that the temperature is adjusted to be the temperature (e.g., 800° C.) at which the solid-electrolyte layers become active.

The upper connector electrode 71 and the lower connector electrode 72 are each disposed on the rear end-side part of any of the side surfaces of the element main body 60. The upper connector electrode 71 and the lower connector electrode 72 are electrodes that enable electrical conduction between the element main body 60 and the outside. The upper and lower connector electrodes 71 and 72 are not covered with the porous layer 80 and exposed to the outside. In this embodiment, four upper connector electrodes 71a to 71d, which serve as an upper connector electrode 71, are arranged in the left-to-right direction and disposed on the rear end-side part of the first surface 60a, and four lower connector electrodes 72a to 72d, which serve as a lower connector electrode 72, are arranged in the left-to-right direction and disposed on the rear end-side part of the second surface 60b (lower surface), which is opposite to the first surface 60a (upper surface). Each of the connector electrodes 71a to 71d and 72a to 72d is in electrical conduction with any of the electrodes 64 to 68 and the heater 69 included in the detection unit 63. In this embodiment, the upper connector electrode 71a is in conduction with the measurement electrode 67; the upper connector electrode 71b is in conduction with the outer electrode 64; the upper connector electrode 71c is in conduction with the inner auxiliary pump electrode 66; the upper connector electrode 71d is in conduction with the inner main pump electrode 65; the lower connector electrodes 72a to 72c are each in conduction with the heater 69; and the lower connector electrode 72d is in conduction with the reference electrode 68. The upper connector electrode 71b and the outer electrode 64 are in conduction with each other via an outer lead wire 75 disposed on the first surface 60a (see FIGS. 3 and 4). Each of the other connector electrodes is in conduction with a corresponding one of the electrodes and the heater 69 via a lead wire, through-hole, or the like formed inside the element main body 60.

The porous layer 80 is a porous body that covers at least the front end-side parts of the side surfaces of the element main body 60 on which the upper and lower connector electrodes 71 and 72 are disposed, that is, the first and second surfaces 60a and 60b. In this embodiment, the porous layer 80 includes an inner porous layer 81 that covers the first and second surfaces 60a and 60b and an outer porous layer 85 disposed on the outer surface of the inner porous layer 81.

The inner porous layer 81 includes a first inner porous layer 83 that covers the first surface 60a and a second inner porous layer 84 that covers the second surface 60b. The first inner porous layer 83 covers the entirety of the region extending from the front end to the rear end of the first surface 60a on which the upper connector electrodes 71a to 71d are disposed, except the regions in which a first water-penetration reduction portion 91 and the upper connector electrode 71 are present (see FIGS. 2 to 4). The width of the first inner porous layer 83 in the left-to-right direction is equal to the width of the first surface 60a in the left-to-right direction. The first inner porous layer 83 covers the region that extends from the left end to the right end of the first surface 60a. The first water-penetration reduction portion 91 divides the first inner porous layer 83 into a front end-side portion 83a located on the front end-side across the first water-penetration reduction portion 91 and a rear end-side portion 83b located on the rear end-side across the first water-penetration reduction portion 91 in the longitudinal direction. The first inner porous layer 83 covers at least a part of the outer electrode 64 and at least a part of the outer lead wire 75. In this embodiment, the first inner porous layer 83 covers the entirety of the outer electrode 64 and the entirety of the part of the outer lead wire 75 on which the first water-penetration reduction portion 91 is not present as illustrated in FIGS. 3 and 4. The first inner porous layer 83 serves as, for example, a protection layer that protects the outer electrode 64 and the outer lead wire 75 from the components of the measurement-object gas, such as sulfuric acid, and suppresses the corrosion and the like of the outer electrode 64 and the outer lead wire 75.

The second inner porous layer 84 covers the entirety of the region extending from the front end to the rear end of the second surface 60b on which the lower connector electrodes 72a to 72d are disposed, except the regions in which a second water-penetration reduction portion 94 and the lower connector electrode 72 are present (see FIGS. 2, 3, and 5). The width of the second inner porous layer 84 in the left-to-right direction is equal to the width of the second surface 60b in the left-to-right direction. The second inner porous layer 84 covers the region that extends from the left end to the right end of the second surface 60b. The second water-penetration reduction portion 94 divides the second inner porous layer 84 into a front end-side portion 84a located on the front end-side across the second water-penetration reduction portion 94 and a rear end-side portion 84b located on the rear end-side across the second water-penetration reduction portion 94 in the longitudinal direction.

The outer porous layer 85 covers the first to fifth surfaces 60a to 60e. The outer porous layer 85 covers the first surface 60a and the second surface 60b as a result of covering the inner porous layer 81. The length of the outer porous layer 85 in the front-to-rear direction is smaller than the length of the inner porous layer 81 in the front-to-rear direction. The outer porous layer 85 covers only the front end of the element main body 60 and a region of the element main body 60 around the front end, unlike the inner porous layer 81. Thus, the outer porous layer 85 covers a part of the element main body 60 which surrounds the electrodes 64 to 68 included in the detection unit 63. In other words, the outer porous layer 85 covers a part of the element main body 60 which is disposed inside the element chamber 33 and exposed to the measurement-object gas. Thereby, the outer porous layer 85 serves as, for example, a protection layer that reduces the likelihood of moisture and the like included in the measurement-object gas adhering to the element main body 60 and causing cracking of the element main body 60.

The porous layer 80 is composed of, for example, a ceramic porous body, such as an alumina porous body, a zirconia porous body, a spinel porous body, a cordierite porous body, a titania porous body, or a magnesia porous body. In this embodiment, the porous layer 80 is composed of an alumina porous body. The thicknesses of the first inner porous layer 83 and the second inner porous layer 84 may be, for example, 5 µm or more and 40 µm or less. The thickness of the outer porous layer 85 may be, for example, 40 µm or more and 800 µm or less. The porosity of the porous layer 80 is 10% or more. Although the porous layer 80 covers the outer electrode 64 and the gas-to-be-analyzed introduction port 61, the measurement-object gas can pass through the porous layer 80 when the porosity of the porous layer 80 is 10% or more. The porosity of the inner porous layer 81 may be 10% or more and 50% or less. The porosity of the outer porous layer 85 may be 10% or more and 85% or less. The outer porous layer 85 may have a higher porosity than the inner porous layer 81.

The porosity of the inner porous layer 81 is determined by the following method using an image (SEM image) obtained by inspecting the inner porous layer 81 with a scanning electron microscope (SEM). First, the sensor element 20 is cut in the thickness direction of the inner porous layer 81 such that a cross section of the inner porous layer 81 can be inspected. The cross section is buried in a resin and ground in order to prepare an observation sample. An image of the observation cross section of the observation sample is taken with a SEM at a 1000 to 10000-fold magnification in order to obtain an SEM image of the inner porous layer 81. Subsequently, the image is subjected to image analysis. A threshold value is determined on the basis of the brightness distribution included in brightness data of pixels of the image by a discriminant analysis method (Otsu's binarization). On the basis of the threshold value, the pixels of the image are binarized into an object portion and a pore portion. The areas of the object portions and the pore portions are calculated. The ratio of the area of the pore portions to the total area (the total area of the object portions and the pore portions) is calculated as a porosity (unit: %). The porosity of the outer porous layer 85 and the porosities of the first and second dense layers 92 and 95, which are described below, are also calculated by the same method as described above.

The water-penetration reduction portion 90 reduces the capillarity of water through the element main body 60 in the longitudinal direction. In this embodiment, the water-penetration reduction portion 90 includes a first water-penetration reduction portion 91 and a second water-penetration reduction portion 94. The first water-penetration reduction portion 91 is disposed on the first surface 60a, on which the upper connector electrode 71 and the first inner porous layer 83 are disposed. As described above, the first water-penetration reduction portion 91 is disposed on the first surface 60a so as to divide the first inner porous layer 83 into front and rear parts in the longitudinal direction. The first water-penetration reduction portion 91 is arranged closer to the front end of the element main body 60 than the upper connector electrode 71, that is, disposed forward of the upper connector electrode 71. The first water-penetration reduction portion 91 is disposed backward of the outer electrode 64. The first water-penetration reduction portion 91 is disposed backward of any of the electrodes 64 to 68 included in the detection unit 63, in addition to the outer electrode 64 (see FIG. 3). The first water-penetration reduction portion 91 is arranged to overlap the insulator 44b in the front-to-rear direction (see FIG. 1). In other words, the region that extends from the front end to the rear end of the first water-penetration reduction portion 91 is included in the region that extends from the front end to the rear end of the insulator 44b. The first water-penetration reduction portion 91 blocks moisture that moves backward inside the front end-side portion 83a by capillarity from passing through the first water-penetration reduction portion 91 and reduces the likelihood of the moisture reaching the upper connector electrode 71. The first water-penetration reduction portion 91 includes a first dense layer 92 and a first gap region 93. The first dense layer 92 is a dense layer having a porosity of less than 10%. The width of the first dense layer 92 in the left-to-right direction is equal to the width of the first surface 60a in the left-to-right direction. The first dense layer 92 covers the first surface 60a so as to extend from the left end to the right end of the first surface 60a. The first dense layer 92 is adjacent to the rear end of the front end-side portion 83a. The first dense layer 92 covers a part of the outer lead wire 75 as illustrated in FIG. 4. The first gap region 93 is a region of the first surface 60a in which the porous layer 80 and the first dense layer 92 are not present. The first gap region 93 is a region between the rear end of the first dense layer 92 and the front end of the rear end-side portion 83b. The outer lead wire 75 is exposed to the outside at a part in which the first gap region 93 is present.

The second water-penetration reduction portion 94 is disposed on the second surface 60b, on which the lower connector electrode 72 and the second inner porous layer 84 are disposed. As described above, the second water-penetration reduction portion 94 is disposed on the second surface 60b so as to divide the second inner porous layer 84 into front and rear parts in the longitudinal direction. The second water-penetration reduction portion 94 is arranged closer to the front end of the element main body 60 than the lower connector electrode 72, that is, disposed forward of the lower connector electrode 72. The second water-penetration reduction portion 94 is disposed backward of the outer electrode 64. The second water-penetration reduction portion 94 is disposed backward of any of the electrodes 64 to 68 included in the detection unit 63, in addition to the outer electrode 64 (see FIG. 3). The second water-penetration reduction portion 94 is arranged to overlap the insulator 44b in the front-to-rear direction (see FIG. 1). In other words, the region that extends from the front end to the rear end of the second water-penetration reduction portion 94 is included in the region that extends from the front end to the rear end of the insulator 44b. The second water-penetration reduction portion 94 blocks moisture that moves backward inside the front end-side portion 84a by capillarity from passing through the second water-penetration reduction portion 94 and reduces the likelihood of the moisture reaching the lower connector electrode 72. The second water-penetration reduction portion 94 includes a second dense layer 95 and a second gap region 96. The second dense layer 95 is a dense layer having a porosity of less than 10%. The width of the second dense layer 95 in the left-to-right direction is equal to the width of the second surface 60b in the left-to-right direction. The second dense layer 95 covers the second surface 60b so as to extend from the left end to the right end of the second surface 60b. The second dense layer 95 is adjacent to the rear end of the front end-side portion 84a. The second gap region 96 is a region of the second surface 60b in which the porous layer 80 and the second dense layer 95 are not present. The second gap region 96 is a region between the rear end of the second dense layer 95 and the front end of the rear end-side portion 84b.

The length L of the first and second water-penetration reduction portions 91 and 94 in the longitudinal direction (see FIGS. 4 and 5) is 0.5 mm or more. When the length L is 0.5 mm or more, the likelihood of the moisture passing through the first and second water-penetration reduction portions 91 and 94 can be reduced to a sufficient degree. The length L may be 5 mm or more. The length L may be 25 mm or less or 20 mm or less. Although the first and second water-penetration reduction portions 91 and 94 have the same length L in this embodiment, they may have different lengths L.

The first and second dense layers 92 and 95 may be composed of any of the ceramics described above as examples of the material for the porous layer 80, although the first and second dense layers 92 and 95 are different from the porous layer 80 in that the porosity of the first and second dense layers 92 and 95 is less than 10%. In this embodiment, the first and second dense layers 92 and 95 are composed of an alumina ceramic. The thickness of the first and second dense layers 92 and 95 may be, for example, 5 µm or more and 40 µm or less. The thickness of the first dense layer 92 is preferably equal to or larger than that of the first inner porous layer 83. Similarly, the thickness of the second dense layer 95 is preferably equal to or larger than that of the second inner porous layer 84. The porosity of the first and second dense layers 92 and 95 is preferably 8% or less and is more preferably 5% or less. The smaller the porosity of the first and second dense layers 92 and 95, the higher the degree of reduction in the capillarity of water in the longitudinal direction of the element main body 60 which is achieved by the first and second dense layers 92 and 95.

The length Le of the first and second dense layers 92 and 95 in the longitudinal direction (see FIGS. 4 and 5) is preferably 0.5 mm or more. In such a case, the likelihood of the moisture passing through the first and second water-penetration reduction portions 91 and 94 in the longitudinal direction can be reduced to a sufficient degree by using only the first and second dense layers 92 and 95, respectively. The length Le may be 5 mm or more. Although the first and second dense layers 92 and 95 have the same length Le in this embodiment, they may have different lengths Le.

The length Lg of the first gap region 93 and the second gap region 96 in the longitudinal direction is preferably 1 mm or less. When the length Lg is relatively small, the area of the parts of the side surfaces (in this embodiment, the first and second surfaces 60a and 60b) of the element main body 60 which are exposed to the outside, that is, the parts of the side surfaces which are not covered with any of the porous layer 80, the first dense layer 92, and the second dense layer 95, can be reduced. In particular, in this embodiment, the outer lead wire 75 is disposed on the first surface 60a, and the outer lead wire 75 is disadvantageously exposed to the outside in the region in which the first gap region 93 is present. Setting the length Lg of the first gap region 93 to be small reduces the area of the part of the outer lead wire 75 which is not covered with any of the porous layer 80 and the first dense layer 92.

The method for producing the gas sensor 10 is described below. First, the method for producing the sensor element 20 is described. In the production of the sensor element 20, first, a plurality of (in this embodiment, six) unbaked ceramic green sheets that correspond to the element main body 60 are prepared. In each of the green sheets, as needed, notches, through-holes, grooves, and the like are formed by punching or the like, and electrodes and wire patterns are formed by screen printing. In addition, unbaked porous layers that are to be formed into the first inner porous layer 83 and the second inner porous layer 84 after baking and unbaked dense layers that are to be formed into the first and second dense layers 92 and 95 after baking are formed on the surfaces of the green sheets which correspond to the first and second surfaces 60a and 60b by screen printing. Subsequently, the green sheets are stacked on top of one another. The green sheets stacked on top of one another are an unbaked element main body that is to be formed into the element main body after baking and include unbaked porous layers and unbaked dense layers. The unbaked element main body is baked to form the element main body 60 including the first inner porous layer 83, the second inner porous layer 84, the first dense layer 92, and the second dense layer 95. Subsequently, the outer porous layer 85 is formed by plasma spraying. Hereby, the sensor element 20 is prepared. For producing the porous layer 80, the first dense layer 92, and the second dense layer 95, gel casting, dipping, and the like can be used in addition to screen printing and plasma spraying.

The gas sensor 10 that includes the sensor element 20 is produced. First, the sensor element 20 is inserted into the cylindrical body 41 so as to penetrate the cylindrical body 41 in the axial direction. Subsequently, the insulator 44a, the compact 45a, the insulator 44b, the compact 45b, the insulator 44c, and the metal ring 46 are disposed in the gap between the inner peripheral surface of the cylindrical body 41 and the sensor element 20 in this order. Then, the metal ring 46 is pressed in order to compress the compacts 45a and 45b. While the compacts 45a and 45b are compressed, the diameter reduction portions 43c and 43d are formed. Hereby, the element-sealing member 40 is produced, and the gap between the inner peripheral surface of the cylindrical body 41 and the sensor element 20 is sealed. The protective cover 30 is welded to the element-sealing member 40, and the nut 47 is attached to the element-sealing member 40. Hereby, the assembly 15 is produced. Lead wires 55 attached to a rubber stopper 57 so as to penetrate the rubber stopper 57 and a connector 50 connected to the lead wires 55 are prepared. The connector 50 is connected to the rear end-side part of the sensor element 20. Subsequently, the external cylinder 48 is fixed to the main fitting 42 by welding. Hereby, the gas sensor 10 is produced.

In the case where the element main body 60, the first dense layer 92, and the second dense layer 95 are formed by baking the unbaked element main body and the unbaked dense layers as described above, the length Le of the first and second dense layers 92 and 95 is preferably 20 mm or less. Since the unbaked element main body and the unbaked dense layers may have different shrinkage ratios during baking, if the length Le is excessively large, the sensor element 20 may become warped during baking. When the length Le is 20 mm or less, the warpage of the sensor element 20 during baking can be limited. The length Le of the first and second dense layers 92 and 95 is preferably 30% or less of the length of the element main body 60 in the longitudinal direction. When the above condition is satisfied, the warpage of the sensor element 20 during baking can also be limited.

An example of the application of the gas sensor 10 is described below. When the measurement-object gas flows inside the pipe 58 while the gas sensor 10 is attached to the pipe 58 as illustrated in FIG. 1, the measurement-object gas passes through the inside of the protective cover 30 and enters the element chamber 33. Consequently, the front end-side part of the sensor element 20 is exposed to the measurement-object gas. Upon the measurement-object gas passing through the porous layer 80, reaching the outer electrode 64, and reaching the inside of the sensor element 20 through the gas-to-be-analyzed introduction port 61, the detection unit 63 generates an electrical signal reflective of the NOx concentration in the measurement-object gas, as described above. The electrical signal is drawn through the upper and lower connector electrodes 71 and 72. The NOx concentration can be determined on the basis of the electrical signal.

The measurement-object gas may contain moisture, which may move inside the porous layer 80 by capillarity. If the moisture reaches the upper and lower connector electrodes 71 and 72, which are exposed to the outside, the water and the components dissolved in the water, such as sulfuric acid, may cause rusting and corrosion of the upper and lower connector electrodes 71 and 72 and a short circuit between some of the upper and lower connector electrodes 71 and 72 which are adjacent to one another. However, in this embodiment, even when the moisture contained in the measurement-object gas moves inside the porous layer 80 (in particular, inside the first inner porous layer 83 and the second inner porous layer 84) toward the rear end-side part of the element main body 60 by capillarity, the moisture reaches the first water-penetration reduction portion 91 or the second water-penetration reduction portion 94 before reaching the upper and lower connector electrodes 71 and 72. The first water-penetration reduction portion 91 includes the first dense layer 92 having a porosity of less than 10% and the first gap region 93 that is a space in which the porous layer is absent, and both of them reduce the capillarity of water in the longitudinal direction of the element main body 60. In addition, since the length L of the first water-penetration reduction portion 91 in the longitudinal direction is 0.5 mm or more, the likelihood of moisture passing through the first water-penetration reduction portion 91 can be reduced to a sufficient degree. By the above mechanisms, the first water-penetration reduction portion 91 reduces the likelihood of the moisture passing through the first water-penetration reduction portion 91 from the front end-side portion 83a-side and reaching the upper connector electrode 71 (the upper connector electrodes 71a to 71d). Therefore, in the sensor element 20, the above-described trouble caused by the water adhering to the upper connector electrode 71 may be reduced. In the similar manner as described above, the second water-penetration reduction portion 94, which includes the second dense layer 95 and the second gap region 96, reduces the likelihood of the moisture passing through the second water-penetration reduction portion 94 from the front end-side portion 84a-side and reaching the lower connector electrode 72 (the lower connector electrodes 72a to 72d). Therefore, in the sensor element 20, the above-described trouble caused by the water adhering to the lower connector electrode 72 may be reduced.

The correspondences between the elements constituting this embodiment and the elements constituting the present invention are explicitly described below: the element main body 60 in this embodiment corresponds to the element main body in the present invention; the detection unit 63 corresponds to the detection unit; the connector electrodes 71a to 71d and 72a to 72d correspond to the connector electrodes; the first surface 60a and the second surface 60b correspond to the side surface on which the connector electrodes are disposed; the porous layer 80 corresponds to the porous layer; the first and second water-penetration reduction portions 91 and 94 each correspond to the water-penetration reduction portion; the outer lead wire 75 corresponds to the outer lead portion; the outer electrode 64 corresponds to the outer electrode; the first surface 60a corresponds to the first side surface; and the second surface 60b corresponds to the second side surface.

Since the sensor element 20 according to this embodiment described above in detail includes the first water-penetration reduction portion 91 disposed on any of the one or more side surfaces (in this embodiment, the first surface 60a) of the element main body 60, the likelihood of the moisture passing through the porous layer 80 (in this embodiment, in particular, the first inner porous layer 83) and reaching the upper connector electrodes 71a to 71d can be reduced. In the same manner as above, since the sensor element 20 includes the second water-penetration reduction portion 94 disposed on any of the one or more side surfaces (in this embodiment, the second surface 60b) of the element main body 60, the likelihood of the moisture passing through the porous layer 80 (in this embodiment, in particular, the second inner porous layer 84) and reaching the lower connector electrodes 72a to 72d can also be reduced.

Since the length Le of the first and second dense layers 92 and 95 is 0.5 mm or more, the likelihood of the moisture passing through the water-penetration reduction portion 90 in the longitudinal direction can be reduced to a sufficient degree by using only the first and second dense layers 92 and 95 of the first and second water-penetration reduction portions 91 and 94, respectively. Since the length Le of the first and second dense layers 92 and 95 is 20 mm or less, the warpage of the sensor element 20 caused due to the difference in shrinkage ratio during baking between the unbaked element main body and the unbaked dense layers can be reduced. Since the length Le of the first and second dense layers 92 and 95 is 30% or less of the length of the element main body 60 in the longitudinal direction, the warpage of the sensor element 20 can be further reduced.

Since the length Lg of the first and second gap regions 93 and 96 is 1 mm or less, that is, relatively small, the area of parts of the side surfaces (in this embodiment, the first and second surfaces 60a and 60b) of the element main body 60 which are exposed to the outside (the parts that are not covered with any of the porous layer 80, the first dense layers 92, and the second dense layer 95) can be reduced.

The sensor element 20 includes an outer lead wire 75 that is disposed on the side surface (in this embodiment, the first surface 60a) on which the upper connector electrode 71 is disposed and that provides electrical conduction between any of the electrodes (in this embodiment, the outer electrode 64) included in the detection unit 63 and the upper connector electrode 71b. The porous layer 80 (in particular, the first inner porous layer 83) covers at least a part of the outer lead wire 75. Consequently, at least a part of the outer lead wire 75 can be protected by the porous layer 80. In the case where the outer lead wire 75 is protected by the porous layer 80, the porous layer (in this embodiment, the first inner porous layer 83) is likely to be formed at a position close to the upper connector electrode 71b. In such a case, it is meaningful to reduce the likelihood of the moisture passing through the first inner porous layer 83 and reaching the upper connector electrode 71b by using the first water-penetration reduction portion 91.

It is to be understand that the present invention is not limited to the above-described embodiment at all, but intended to include a variety of forms within the technical scope of the present invention.

Figure 6:
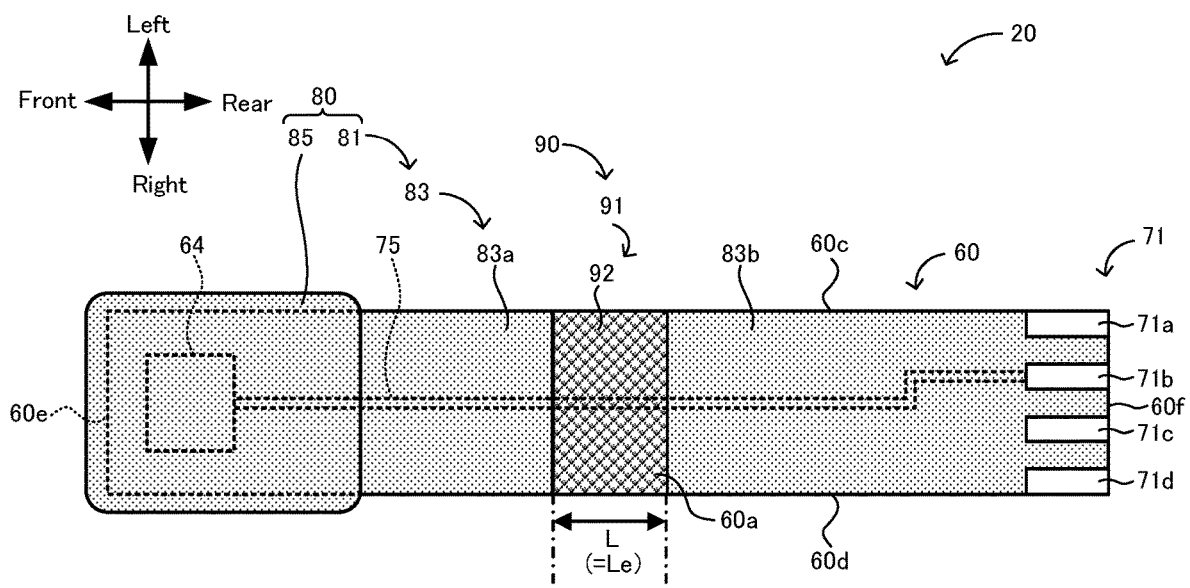
FIG. 6 is a top view of a modification example of a sensor element 20.

For example, although the first water-penetration reduction portion 91 includes the first dense layer 92 and the first gap region 93 in the above-described embodiment, the first water-penetration reduction portion 91 includes at least the first dense layer 92. That is, the first water-penetration reduction portion 91 does not necessarily include the first gap region 93. In other words, the length Lg in the first water-penetration reduction portion 91 may be 0 mm. FIG. 6 is a top view of such a sensor element 20. When the first water-penetration reduction portion 91 does not include the first gap region 93, the area of a part of the first surface 60a which is exposed to the outside (the portion that is not covered with any of the porous layer 80 and the first dense layer 92) can be further reduced. The same applies to the second water-penetration reduction portion 94.

Although the first water-penetration reduction portion 91 divides the first inner porous layer 83 into the front end-side portion 83a and the rear end-side portion 83b in the longitudinal direction in the above-described embodiment, the present invention is not limited to this. The first water-penetration reduction portion 91 may be arranged closer to the rear end than the porous layer 80. For example, in the above-described embodiment, the first inner porous layer 83 does not necessarily include the rear end-side portion 83b. In such a case, the region in which the rear end-side portion 83b is disposed in FIG. 4 is considered a part of the first gap region 93. Similarly to the first water-penetration reduction portion 91, the second water-penetration reduction portion 94 may be arranged closer to the rear end than the porous layer 80 instead of dividing the second inner porous layer 84 into two parts.

Although the first dense layer 92 is disposed forward of the first gap region 93 so as to be adjacent to the first gap region 93 in the above-described embodiment, the first dense layer 92 may be disposed backward of the first gap region 93 so as to be adjacent to the first gap region 93. The same applies to the second water-penetration reduction portion 94.

Although the first and second water-penetration reduction portions 91 and 94 are arranged to overlap the insulator 44b in the front-to-rear direction in the above-described embodiment, the present invention is not limited to this. For example, the first and second water-penetration reduction portions 91 and 94 may be arranged to overlap the insulator 44a or the insulator 44c in the front-to-rear direction or may be disposed backward of the metal ring 46. The first and second water-penetration reduction portions 91 and 94 are preferably disposed so as not to be exposed to the inside of the element chamber 33.

In the above-described embodiment, the sensor element 20 does not necessarily include the second inner porous layer 84 and the second surface 60b is not necessarily covered with the porous layer 80. In such a case, the sensor element 20 does not necessarily include the second water-penetration reduction portion 94. The water-penetration reduction portion may be disposed on at least one of the side surfaces of the element main body (in the above-described embodiment, the first to fourth surfaces 60a to 60d) on which the connector electrodes and the porous protection layer are disposed (in the above-described embodiment, the first and second surfaces 60a and 60b). This reduces the likelihood of the moisture reaching the connector electrodes at least on the side surface on which the water-penetration reduction portion is disposed.

Although the first inner porous layer 83 covers the region that extends from the front to rear ends of the first surface 60a except the region in which the first water-penetration reduction portion 91 and the upper connector electrode 71 are present in the above-described embodiment, the present invention is not limited to this. For example, the first inner porous layer 83 may cover a region that extends from the front end of the first surface 60a to the front end-side ends of the upper connector electrodes 71a to 71d except the region in which the first water-penetration reduction portion 91 is present. Alternatively, the first inner porous layer 83 may cover at least a region that extends from the front end of the first surface 60a to the rear of the first water-penetration reduction portion 91 except the region in which the first water-penetration reduction portion 91 is present. The same applies to the second inner porous layer 84.

Although the element main body 60 has a rectangular cuboid shape in the above-described embodiment, the present invention is not limited to this. For example, the element main body 60 may have a hollow cylindrical shape or a solid cylindrical shape. In such a case, the element main body 60 has one side surface.

EXAMPLES

Example cases where a specific sensor element was prepared are described below as Examples. Experimental examples 5 to 7, 9, 10, 12 to 14, 16 to 18, 20, 21, 23, 24, 26, 27, 29, and 30 correspond to Examples of the present invention, while Experimental examples 1 to 4, 8, 11, 15, 19, 22, 25, 28, and 31 correspond to Comparative examples. Note that the present invention is not limited by Examples below.

Experimental Example 1

In Experimental example 1, a sensor element that was the same as the sensor element 20 illustrated in FIGS. 2 to 5, except that the sensor element did not include the first water-penetration reduction portion 91, the second water-penetration reduction portion 94, and the outer porous layer 85, was prepared. That is, in Experimental example 1, the first and second inner porous layers 83 and 84 were arranged to cover the entirety of the first and second surfaces 60a and 60b except the region in which the upper and lower connector electrodes 71 and 72 were disposed. The sensor element 20 of the Experimental example 1 was prepared in the following manner. First, zirconia particles containing 4 mol % yttria serving as a stabilizer were mixed with an organic binder and an organic solvent. The resulting mixture was formed into six ceramic green sheets by tape casting. Patterns of electrodes and the like were printed in each of the green sheets. In addition, unbaked porous layers that were to be formed into the first inner porous layer 83 and the second inner porous layer 84 after baking were formed by screen printing. The unbaked porous layers were composed of a slurry prepared by mixing a raw-material powder (an alumina powder), a binder solution (polyvinyl acetal and butyl carbitol), a solvent (acetone), and a pore-forming material with one another. Subsequently, the six green sheets were stacked on top of one another and baked in order to prepare the element main body 60 including the first and second inner porous layers 83 and 84. Hereby, the sensor element 20 of Experimental example 1 was prepared. The dimensions of the element main body 60 were 67.5 mm long, 4.25 mm wide, and 1.45 mm thick. The first and second inner porous layers 83 and 84 had a thickness of 20 μm and a porosity of 30%.

Experimental Examples 2 to 31

In Experimental examples 2 to 31, a sensor element that was the same as that prepared in Experimental example 1, except that the sensor element included the first and second water-penetration reduction portions 91 and 94, was prepared. In Experimental examples 2 to 31, the length Le and the porosity of the first and second dense layers 92 and 95, the length Lg of the first and second gap regions 93 and 96, and the length L of the first and second water-penetration reduction portions 91 and 94 were changed as described in Table 1. The unbaked dense layers that were to be formed into the first and second dense layers 92 and 95 after baking were formed using a slurry that was the same as that used for forming the unbaked porous layers in Experimental example 1, except that the amount of the pore-forming material added to the slurry was reduced. In Experimental examples 2 to 31, the porosity of the first and second dense layers 92 and 95 was changed by adjusting the amount of the pore-forming material added to the slurry. In Experimental examples 2 to 31 except Experimental example 5, the first water-penetration reduction portion 91 did not include the first gap region 93 and the second water-penetration reduction portion 94 did not include the second gap region 96 as illustrated in FIG. 6. In Experimental examples 2 to 31, the first and second dense layers 92 and 95 had a thickness of 20 μm. In Experimental examples 2 to 31, the front ends of the first and second water-penetration reduction portions 91 and 94 were located at a position 26 mm from the front end of the element main body 60.

[Liquid Penetration Test]

Each of the sensor elements 20 prepared in Experimental examples 1 to 31 was tested in order to determine the amount of liquid that penetrated the rear end-side part of the element main body 60 by capillarity when the front end-side part of the element main body 60 was immersed in the liquid. First, while the sensor element 20 was held such that the longitudinal direction of the sensor element 20 was parallel to the vertical direction, a part of the sensor element 20 which extended from the front end (fifth surface 60e) of the element main body 60 to a position (hereinafter, "immersion position") 20 mm from the front end toward the rear end was immersed into a red-check solution. While the sensor element was immersed in the red-check solution, the sensor element was left to stand for 20 hours. Subsequently, the distance the red-check solution penetrated from the immersion position toward the rear end was measured visually as a penetration distance. The penetration distance indicates the distance the red-check solution moved from the immersion position toward the rear end of the element main body 60 inside the first and second inner porous layers 83 and 84 by capillarity. An evaluation grade of Excellent (A) was given when the penetration distance measured after a lapse of 20 hours was less than 10 mm. An evaluation grade of Good (B) was given when the penetration distance measured after a lapse of 20 hours was 10 mm or more and less than 20 mm. An evaluation grade of Failure (F) was given when the penetration distance measured after a lapse of 20 hours was 20 mm or more. The red-check solution used was "R-3B (NT) PLUS" produced by Eishin Kagaku Co., Ltd. The red-check solution included 40 to 60 wt % hydrocarbon oil, 10 to 20 wt % plastic solvent, 1 to 20 wt % glycol ether, 12 to 50 wt % non-ionic surfactant, and 1 to 5 wt % oil-soluble azo red dye. The red-check solution had a density of 0.86 g/cm$^3$ at 20° C., which was lower than the density of water.

[Evaluation of Warpage of Sensor Element]

The amount of warpage of each of the sensor elements 20 prepared in Experimental examples 1 to 31 in the thickness direction (top-to-bottom direction) of the sensor element 20 was measured with a laser displacement sensor "LK-010" produced by Keyence Corporation. In Experimental example 1, 100 sensor elements 20 were prepared, and the amount of warpage of each of the 100 sensor elements was measured. When the amount of warpage of a sensor element was 200 μm or more, the sensor element was considered warped. The number of warped sensor elements of the 100 sensor elements was counted, and the warpage occurrence rate was calculated. In Experimental examples 2 to 31, the warpage occurrence rate was calculated as in Experimental example 1. An evaluation of Excellent (A) was given when the warpage occurrence rate was less than 1% (any of the 100 sensor elements did not become warped). An evaluation of Good (B) was given when the warpage occurrence rate was 1% or more and less than 20%. An evaluation of Failure (F) was given when the warpage occurrence rate was 20% or more.

Figure 7:
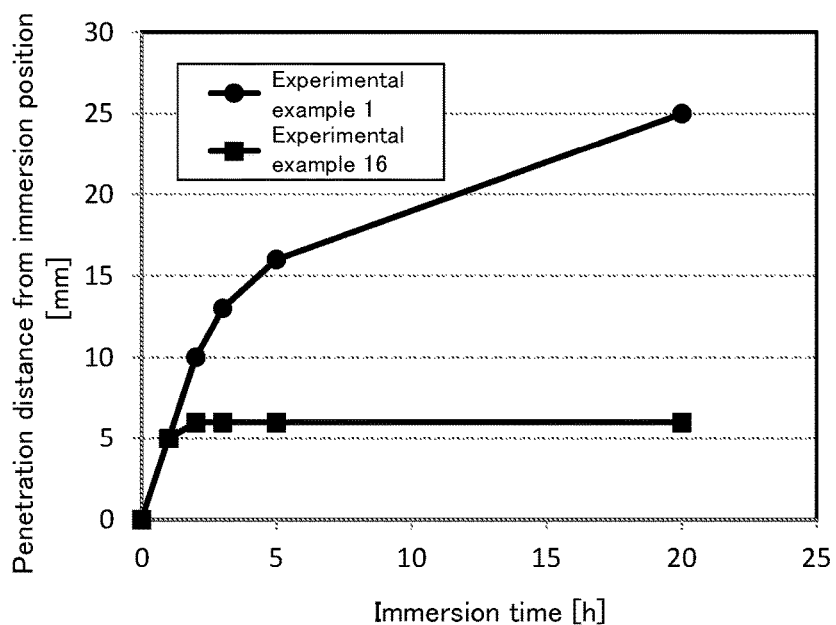
FIG. 7 is a graph illustrating changes in penetration distance with time which were measured in liquid penetration tests conducted in Experimental examples 1 and 16.

Table 1 summarizes the length Le, the porosity of the first and second dense layers 92 and 95, the length Lg, the length L, the results of evaluation of the liquid penetration test, and the results of evaluation of warpage of the sensor element 20 in each of Experimental examples 1 to 31. FIG. 7 is a graph illustrating changes in penetration distance with time which were measured in the liquid penetration tests conducted in Experimental examples 1 and 16.

TABLE 1

| | Length Le of dense layer [mm] | Porosity of dense layer [%] | Length Lg of gap region [mm] | Length L of water-penetration reduction portion (= Le + Lg)[mm] | Liquid penetration test | Warpage of sensor element |
|---|---|---|---|---|---|---|
| Experimental example 1 | 0 | — | 0 | 0 | F | A |
| Experimental example 2 | 0.3 | 0 | 0 | 0.3 | F | A |
| Experimental example 3 | | 5 | | | F | A |
| Experimental example 4 | | 10 | | | F | A |
| Experimental example 5 | | 0 | 0.2 | 0.5 | A | A |
| Experimental example 6 | 0.5 | 0 | 0 | 0.5 | A | A |
| Experimental example 7 | | 5 | | | B | A |
| Experimental example 8 | | 10 | | | F | A |
| Experimental example 9 | 1 | 0 | 0 | 1 | A | A |
| Experimental example 10 | | 5 | | | B | A |
| Experimental example 11 | | 10 | | | F | A |
| Experimental example 12 | 3 | 0 | 0 | 3 | A | A |
| Experimental example 13 | | 5 | | | A | A |
| Experimental example 14 | | 8 | | | B | A |
| Experimental example 15 | | 10 | | | F | A |
| Experimental example 16 | 5 | 0 | 0 | 5 | A | A |
| Experimental example 17 | | 5 | | | A | A |
| Experimental example 18 | | 8 | | | B | A |
| Experimental example 19 | | 10 | | | F | A |
| Experimental example 20 | 10 | 0 | 0 | 10 | A | A |
| Experimental example 21 | | 5 | | | A | A |
| Experimental example 22 | | 10 | | | F | A |
| Experimental example 23 | 15 | 0 | 0 | 15 | A | A |
| Experimental example 24 | | 5 | | | A | A |
| Experimental example 25 | | 10 | | | F | A |
| Experimental example 26 | 20 | 0 | 0 | 20 | A | B |
| Experimental example 27 | | 5 | | | A | B |
| Experimental example 28 | | 10 | | | F | A |
| Experimental example 29 | 27 | 0 | 0 | 27 | A | F |
| Experimental example 30 | | 5 | | | A | F |
| Experimental example 31 | | 10 | | | F | F |

The results illustrated in FIG. 7 show that, in Experimental example 1 where the first and second water-penetration reduction portions 91 and 94 were absent, the penetration distance was increased with time. This confirms that the red-check solution moved inside the first and second inner porous layers 83 and 84 toward the rear of the sensor element 20 by capillarity. In contrast, in Experimental example 16 where the first and second water-penetration reduction portions 91 and 94 were present, the red-check solution reached a penetration position of 6 mm (=the position 26 mm from the front end of the element main body 60) that was the position of the front ends of the first and second water-penetration reduction portions 91 and 94. This confirms that, in Experimental example 16, the first and second water-penetration reduction portions 91 and 94 blocked the red-check solution from moving backward by capillarity.

The results described in Table 1 show that, in Experimental examples 5 to 7, 9, 10, 12 to 14, 16 to 18, 20, 21, 23, 24, 26, 27, 29, and 30 where the length L was 0.5 mm or more and the porosity of the first and second dense layers 92 and 95 was less than 10%, the results of the liquid penetration test were evaluated as Excellent or Good. In contrast, in Experimental examples 1 to 4 where the length L was less than 0.5 mm and Experimental examples 8, 11, 15, 19, 22, 25, 28, and 31 where the porosity of the first and second dense layers 92 and 95 was 10%, the results of the liquid penetration test were evaluated as Failure. This confirms that, when length L of the first and second water-penetration reduction portions 91 and 94 is 0.5 mm or more and the porosity of the first and second dense layers 92 and 95 is less than 10%, the movement of the moisture by capillarity can be reduced by the first and second water-penetration reduction portions 91 and 94 to a sufficient degree. The results obtained in Experimental example 5 show that, even in the case where the length Le of the first and second dense layers 92 and 95 was less than 0.5 mm, the movement of the moisture by capillarity was suppressed to a sufficient degree when the length L of the first and second water-penetration reduction portions 91 and 94 was 0.5 mm or more. A comparison between Experimental examples 6 and 7 and a comparison among Experimental examples 12 to 14 confirm that, the lower the porosity of the first and second dense layers 92 and 95, the greater the suppression of the movement of the moisture by capillarity. It was also confirmed that, the larger the length Le of the first and second dense layers 92 and 95, the lower the likelihood of the evaluation grade of the liquid penetration test being lowered from A to B even when the porosity of the first and second dense layers 92 and 95 is high.

The results described in Table 1 show that, in Experimental examples 29 to 31 where the length Le of the first and second dense layers 92 and 95 was more than 20 mm (=the length Le was 40% of the length (67.5 mm) of the element main body 60), the sensor element 20 was likely to become warped, and an evaluation grade of Failure was given. In Experimental examples 1 to 28 where the length Le was 20 mm or less (the length Le was 30% or less of the length (67.5 mm) of the element main body 60), an evaluation grade of "A" or "B" was given. This confirms that the warpage of the sensor element 20 was reduced. It was also confirmed that, the smaller the length Le, the lower the likelihood of the sensor element 20 becoming warped.

What is claimed is:
1. A sensor element comprising:
   a long-length element main body including front and rear ends and one or more side surfaces, the front and rear ends being ends of the element main body in a longi- tudinal direction of the element main body, the one or more side surfaces being surfaces extending in the longitudinal direction;
a detection unit including a plurality of electrodes disposed in the front end-side part of the element main body, the detecting unit detecting a specific gas concentration in a measurement-object gas;
one or more connector electrodes disposed on the rear end-side part of any of the one or more side surfaces, the one or more connector electrodes used for electrical connection to outside of the sensor element;
a porous layer that covers at least the front end-side part of the one or more side surface on which the one or more connector electrodes are disposed, the porous layer having a porosity of 10% or more; and
a water-penetration reduction portion disposed on the one or more side surfaces so as to divide the porous layer in the longitudinal direction or to be located closer to the rear end than the porous layer, the water-penetration reduction portion being located closer to the front end than the one or more connector electrodes, a length (L) of the water-penetration reduction portion in the longitudinal direction being 0.5 mm or more, the water-penetration reduction portion including a dense layer covering the one or more side surfaces and having a porosity of less than 10% and a gap region in which the porous layer is absent, the gap region being arranged adjacent to the dense layer and at least the dense layer reducing capillarity of water in the longitudinal direction, and the dense layer and a portion of the porous layer located closer to the front end than the dense layer are adjacent to each other, or the dense layer and the portion of the porous layer are separated from each other with the gap region disposed in between.

2. The sensor element according to claim 1, wherein a length (Le) of the dense layer in the longitudinal direction is 0.5 mm or more.

3. The sensor element according to claim 1, wherein a length (Le) of the dense layer in the longitudinal direction is 20 mm or less.

4. The sensor element according to claim 1, wherein a length (Lg) of the gap region in the longitudinal direction is 1 mm or less.

5. The sensor element according to claim 1, further comprising an outer lead portion disposed on the side surface on which the one or more connector electrodes are disposed, the outer lead portion providing electrical conduction between any of the plurality of electrodes and one of the one or more connector electrodes,
wherein the porous layer covers at least a part of the outer lead portion.

6. The sensor element according to claim 1, wherein the porous layer covers at least a region of the side surface on which the one or more connector electrodes are disposed, the region extending from the front end of the side surface to the front end-side edges of the one or more connector electrodes, the region excluding a region in which the water-penetration reduction portion is present, and
the water-penetration reduction portion is disposed on the side surface so as to divide the porous layer in the longitudinal direction.

7. The sensor element according to claim 1, wherein the element main body has a rectangular cuboid shape with four side surfaces that are the one or more side surfaces extending in the longitudinal direction,
wherein the one or more connector electrodes are disposed on each of first and second side surfaces of the four side surfaces, the first and second side surfaces facing each other,
the porous layer covers each of the first and second side surfaces, and
the water-penetration reduction portion is disposed on each of the first and second side surfaces.

8. A gas sensor comprising the sensor element according to claim 1.

9. A sensor element comprising:
a long-length element main body including front and rear ends and one or more side surfaces, the front and rear ends being ends of the element main body in a longitudinal direction of the element main body, the one or more side surfaces being surfaces extending in the longitudinal direction;
a detection unit including a plurality of electrodes disposed in the front end-side part of the element main body, the detecting unit detecting a specific gas concentration in a measurement-object gas;
one or more connector electrodes disposed on the rear end-side part of any of the one or more side surfaces, the one or more connector electrodes used for electrical connection to outside of the sensor element;
a porous layer that covers at least the front end-side part of the one or more side surfaces on which the one or more connector electrodes are disposed, the porous layer having a porosity of 10% or more; and
a water-penetration reduction portion disposed on the one or more side surfaces so as to divide the porous layer in the longitudinal direction or to be located closer to the rear end than the porous layer, the water-penetration reduction portion being located closer to the front end than the one or more connector electrodes, a length (L) of the water-penetration reduction portion in the longitudinal direction being 0.5 mm or more, the water-penetration reduction portion including a dense layer covering the one or more side surfaces and having a porosity of less than 10%, at least the dense layer reducing capillarity of water in the longitudinal direction and the dense layer and a portion of the porous layer located closer to the front end than the dense layer are adjacent to each other.

10. A sensor element according to claim 9, wherein a length (Le) of the dense layer in the longitudinal direction is 0.5 mm or more.

11. A sensor element according to claim 9, wherein a length (Le) of the dense layer in the longitudinal direction is 20 mm or less.

12. A sensor element according to claim 9, wherein the sensor element further includes an outer lead portion disposed on the side surface on which the one or more connector electrodes are disposed, the outer lead portion providing electrical conduction between any of the plurality of electrodes and one of the one or more connector electrodes, and
wherein the porous layer covers at least a part of the outer lead portion.

13. A sensor element according to claim 9, wherein the porous layer covers at least a region of the side surface on which the one or more connector electrodes are disposed, the region extending from the front end of the side surface to the front end-side edges of the one or more connector electrodes, the region excluding a region in which the water-penetration reduction portion is present, and wherein the water-penetration reduction portion is disposed on the side surface so as to divide the porous layer in the longitudinal direction.

14. A sensor element according to claim 9,
wherein the element main body has a rectangular cuboid shape with four side surfaces that are the one or more side surfaces extending in the longitudinal direction,
wherein the one or more connector electrodes are disposed on each of first and second side surfaces of the four side surfaces, the first and second side surfaces facing each other,
wherein the porous layer covers the first and second side surfaces, and
wherein the water-penetration reduction portion is disposed on each of the first and second side surfaces.

15. A gas sensor comprising the sensor element according to claim 9.

* * * * *